(12) United States Patent
Goshe et al.

(10) Patent No.: US 6,818,454 B2
(45) Date of Patent: Nov. 16, 2004

(54) PHOSPHOPROTEIN BINDING AGENTS AND METHODS OF THEIR USE

(75) Inventors: Michael B. Goshe, Richland, WA (US); Thomas P. Conrads, Richland, WA (US); Timothy D. Veenstra, West Richland, WA (US); Ellen A. Panisko, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 217 days.

(21) Appl. No.: 09/788,286

(22) Filed: Feb. 16, 2001

(65) Prior Publication Data

US 2002/0119505 A1 Aug. 29, 2002

(51) Int. Cl.[7] .............................. C07K 1/22; C07K 1/36; C07K 1/13; C07K 1/113; C07K 17/06; C07K 17/14; G01N 24/00; G01N 33/483

(52) U.S. Cl. ........................... 436/173; 436/56; 436/57; 436/86; 530/408; 530/409; 530/412; 530/413; 530/410; 530/811; 530/804

(58) Field of Search ................................ 530/408, 409, 530/413, 410, 811, 804, 412, 812; 436/56, 57, 86, 173, 545

(56) References Cited

U.S. PATENT DOCUMENTS

| 5,686,310 A | 11/1997 | Haystead et al. |
| 2002/0049307 A1 * | 4/2002 | Aebersold et al. |
| 2002/0115056 A1 * | 8/2002 | Goodlett |

FOREIGN PATENT DOCUMENTS

| WO | 00/11208 | 3/2000 |

OTHER PUBLICATIONS

M. Adamczyk et al, Rapid Communication in Mass Spectrometry (2001), 15(16), 1481–1488. Selective analysis of phosphopeptides within a protein mixture by chemical modification, reversible biotinylation and mass spectrometry.*

Clark et al., "Chemical Modification of Phosvitin: Preparation of Dimethylaminovitin and Methylmercaptovitin and their Utility for Elucidation of Phosvitin Primary Structure," *Int. J. Biochem*, 11:577–585, 1967.

Fadden et al., "Quantitative and Selective Fluorophore Labeling of Phosphoserine on Peptides and Proteins: Characterization at the Attomole Level by Capillary Electrophoresis and Laser–Induced Fluorescence," *Anal Biochem*, 225(1):81–88, 1995.

Gygi et al., "Quantitative analysis of complex protein mixtures using isotope–coded affinity tags," *Nature Biotechnology*, 17:994–999, 1999.

Jaffe et al., "Characterization of Serine and Threonine Phosphorylation Sites in β–Elimination/Ethanethiol Addition––Modified Proteins by Electrospray Tandem Mass Spectrometry and Database Searching," *Biochemistry*, 37:16211–16224, 1998.

Mega et al., "Studies on the Methods for Determination of Phosphorylation Sites in Highly Phosphorylated Peptides or Proteins: Phosphorylation Sites of Hen Egg White Riboflavin Binding Protein," *J. Biochem.*, 100:1109–1116, 1986.

Meyer et al., "Sequence analysis of phosphoserine–containing peptides," *FEBS Lett*, 204(1):61–66, 1986.

Weckwerth et al., "Comparative quantification and identification of phosphoproteins using stable isotope labeling and liquid chromatography/mass spectrometry," *Rapid Commun. Mass Spectrom.*, 14:1677–1681, 2000.

Salh et al., "Differential cyclin–dependent kinase expression and activation in human colon cancer," *Anticancer Res*, 19(1B) 741–748, 1999 (Abstract).

Vanmechelen et al., "Quantification of tau phosphorylated at threonine 181 in human cerebrospinal fluid: a sandwich ELISA with a synthetic phosphopeptide for standardization," *Neurosci Lett*, 285(1):49–52, 2000 (Abstract).

Thorpe et al., "Utilizing the Peptidyl–Prolyl Cis–Trans Isomerase Pin 1 as a Probe of Its Phosphorylated Target Proteins. Examples of binding to nuclear proteins in a human kidney cell line and to tau in alzheimer's diseased brain," *J. Histochem Cytochem*, 49(1):97–108, 2001 (Abstract).

Nakayama et al., "Expression and phosphorylation status of retinoblastoma protein in adult T–cell leukemia/lymphoma," *Leuk Res*, 24(4)299–305, 2000 (Abstract).

* cited by examiner

*Primary Examiner*—Mary E. Ceperley
(74) *Attorney, Agent, or Firm*—Klarquist Sparkman, LLP (57) ABSTRACT

The invention provides reagents and methods for characterizing (i.e., identification and/or quantitation) the phosphorylation states of proteins. Proteins may be post-transcriptionally modified such that they contain phosphate groups at either some or all of their serine, threonine, tyrosine, histidine, and/or lysine amino acid residues. In many cases the extent to which a protein is phosphorylated determines it bioactivity, i.e., its ability to effect cell functions such as differentiation, division, and metabolism. Hence, a powerful tool for diagnosing various diseases and for furthering the understanding of protein—protein interactions is provided.

18 Claims, 6 Drawing Sheets

PHOSPHOPROTEIN BINDING AGENTS AND METHODS OF THEIR USE

STATEMENT OF GOVERNMENTAL SUPPORT

This invention was made with United States Government support under Contract DE-AC0676RLO1830 awarded by the U.S. Department of Energy. The United States Government has certain rights in the invention.

FIELD OF THE INVENTION

The invention relates to reagents and methods for detecting and/or quantifying the phosphorylation state and/or level of proteins in samples.

BACKGROUND OF THE INVENTION

The availability of complete genome sequences is moving biological research to an era where cellular systems are analyzed as a whole rather than analyzing the individual components. While genome sequences and global gene expression measurements at the mRNA level opens the door to important biological advances, much of the understanding of cellular systems and the roles of the constituents will arise from proteomics (Wasinger et al., Electrophoresis 16:1090–1094, 1995). Proteomics, the analysis of the entire complement of proteins expressed by a cell, tissue type, or organ, provides the most informative characterization of the cell because proteins are the primary players that carry out nearly all processes within the cell. A key aspect to successful proteomic measurements is the ability to precisely measure protein abundance changes in a high throughput manner so as to allow the effects of many "perturbations" upon, or changes to, a cell type, tissue type or organ, to be determined in a rapid fashion (Pafterson, Curr. Opin. Biotechnol. 11:413–418, 2000). An inherent goal of proteomic studies is to provide a greater understanding of the function of proteins in a global, cellular context, along with the more conventionally delineated molecular function. A greater understanding at the level of cellular systems will provide, for example, a stronger basis for understanding complex biological pathways and the nature of diseases. The global understanding of cellular systems provided by proteomic investigations will provide numerous opportunities unlikely to originate from the present paradigm of "single" protein characterization methodologies.

Though methods to allow global measurements of gene expression at the mRNA level have been developed (Schena et al., Science 270:467–470, 1995 and Khodursky et al., Proc. Natl. Acad. Sci. USA 97:12170–12175, 2000), such methods do not provide direct measurements of protein abundance (Gygi et al., Proc. Natl. Acad. Sci. USA 97:9390–9395, 2000). Clearly, only global analysis of gene expression at the protein level provides information about the roles of individual gene products and their involvement in cellular pathways. Information relating solely to the abundance of a particular protein within a cell fails to provide information relating to the "processed state" of the protein. The "processed state" refers to the level and/or type of post-translational modifications that are displayed by the functional protein. For example many proteins are initially translated in an inactive form and upon subsequent proteolysis, the addition of sugar moieties, phosphate groups, methyl groups, carboxyl groups, or other additional groups so they gain biological function. Information relating to the "processed state" of a given protein is necessary and, hence, methods of detecting the active state of proteins are important for furthering the understanding of intercellular signaling and for developing new and useful interventions and therapeutics.

The reversible phosphorylation of proteins plays a key role in transducing extracellular signals into the cell. Many proteins that participate in cell signaling pathways are phosphorylated via enzymes known as kinases and dephosphorylated via phosphatases. Phosphate groups are added to, for example, tyrosine, serine, threonine, histidine, and/or lysine amino acid residues depending on the specificity of the kinase acting upon the target protein. To date several disease states have been linked to the abnormal phosphorylation/dephosphorylation of specific proteins. For example, the polymerization of phosphorylated tau protein allows for the formation of paired helical filaments that are characteristic of Alzheimer's disease, and the hyperphosphorylation of retinoblastoma protein (pRB) has been reported to progress various tumors (Vanmechelen et al. Neurosci. Lett. 285:49–52, 2000, and Nakayama et al. Leuk. Res. 24:299–305, 2000, respectively).

The ability to quickly screen for irregularties in the phosphorylation state of proteins will further the understanding of intra and inter cellular signaling and lead to the development of improved diagnostics for the detection of various disease states.

SUMMARY OF THE INVENTION

The present disclosure provides reagents and methods for characterizing the phosphorylation state and/or level of a protein. Proteins can be post-transcriptionally modified such that they contain phosphate groups at either some, or all serine, threonine, tyrosine, histidine, and/or lysine amino acid residues. In many cases the extent to which a protein is phosphorylated determines it bioactivity, i.e., its ability to effect cell functions such as differentiation, division, and metabolism. Hence, the present disclosure provides powerful methods for diagnosing various diseases and for furthering the understanding of protein—protein interactions.

One aspect of the invention provides methods of comparing the phosphorylation state of one or more proteins in two or more samples. Moreover, the disclosed methods allow for the generation of phosphorylation profiles, which detect changes in the phosphorylation states of individual proteins within samples, rather than merely detecting overall increases in the phosphorylation level of all of the proteins within a sample. These methods involve providing a substantially chemically identical and differentially isotopically labeled protein reactive reagent for each sample wherein the protein reactive reagent satisfies the formula:

B-L-PhRG wherein B is a binding agent that selectively binds to a capture reagent (CR), L is a linker group having one or more atoms that are differentially labeled with one or more isotopes, and PhRG is a phosphate reactive group that selectively reacts with amino acid residues that were formerly phosphorylated. Each sample is then reacted with one of the protein reactive reagents to provide proteins bound to the protein reactive agent, whereby the bound proteins are differentially labeled with the isotopes. The bound proteins of the samples are captured using the capture reagent that selectively binds the binding agent and the captured bound protein is then subsequently released from the capture reagent by disrupting the interaction between the binding agent and the capture reagent. The released, bound protein is then detected.

Another aspect of the invention provides methods for screening for therapeutics that alter the phosphorylation state of one or more proteins. These methods involve contacting at least one test sample containing a protein with the therapeutic and providing at least one control sample also containing an amount of the protein. One or more phosphate groups from one or more of the amino acid residues in the proteins in the test sample and control sample are removed and the proteins in both the test sample and the control are tagged with isotopically distinguishable B-L-PhRG that are substantially chemically identical. The level of phosphorylation can then be detected in the at least one test sample and the at least one control sample and the ability of the therapeutic to alter the phosphorylation of the protein can be determined.

Another aspect of the invention provides methods of comparing the level of tyrosine, serine, and threonine phosphorylation states of one or more proteins from two or more samples. Generally, these methods are practiced by sequentially removing phosphate groups from either the tyrosine residues, or the serine and threonine residues (the phosphate groups can be removed from either the serine and threonine first or the tyrosine phosphate groups can be removed first). Regardless of which phosphate group is removed first, a differentially isotopically labeled B-L-PhRG is subsequently used to "tag" the protein at the site formerly occupied by the phosphate group. The term "isotopically labeled" means that the L in the B-L-PhRG contains from about 0 to about 400, from about 1 to 300, from about 1 to about 250, from about 1 to about 200, from about 1 to about 150, from about 1 to 100, or from about 1 to about 50, isotopically different atoms. For example, the L will contain from about 0 to about 50 deuterium atoms substituted for hydrogen atoms. Thus the term "differentially isotopically labeled" refers to the fact that when two or more proteins, or two or more samples, are compared, each will be tagged with a B-L-PhRG complex that is isotopically distinguishable from the B-L-PhRG used to label the other protein, or the other sample. Hence, in the example above the serine and threonine residues from the first sample could, for example, be tagged with a B-L-PhRG that contains $HSCH_2CH_2CH_2SH$ and a second sample could, for example, be tagged with a B-L-PhRG that contains $HSCD_2CD_2CD_2SH$. In another embodiment, the tyrosine residues from the first sample could be tagged with a B-L-PhRG that contains $HSCH_2CH_2SH$ and a second sample could be tagged with a B-L-PhRG that contains $HSCD_2CD_2SH$.

Additionally the B of the B-L-PhRG could be chosen such that it was captured by different capture reagents. For example, allowing the tagged tyrosine residues to be captured in a first column chromatography step and the serine and threonine residues to be captured by a second column chromatography step.

The methods described herein can be applied to peptides (fragments of proteins) that are generated via enzymatic or chemical processing. The methods described herein can be also followed by protein sequencing via tandem mass spectrometry, chromatographic separation, or other suitable methods now known or developed in the future for such sequencing. Additionally, standards of known amounts of differentially isotopically labeled proteins can be introduced such that they provide an internal standard that aids in protein and/or peptide quantification.

The methods of this invention can also be used to identify and/or detect a plurality of proteins in a single sample.

Moreover, the methods described herein can be used to compare relative amounts of one or more proteins in two or more samples by individually tagging one or more proteins from two or more samples with isotopically distinguishable B-L-PhRG complexes and then combining the tagged proteins into one sample. The combined sample is then captured, isolated and the differentially isotopically labeled proteins are detected and/or quantified.

The methods described herein are especially useful for quantifying the phosphorylation state of membrane proteins, proteins originating from different organelles, and proteins from different subcellular fractions. Similarly, the methods described herein can be used to determine the phosphorylation state of proteins that results from treatment of samples with different environmental or nutritional conditions, different chemical or physical stimuli or at different times. In some cases, the difference in the phosphorylation state of a protein may be the result of the protein's phosphorylation state in different disease states.

The binding agent can also be used to bind to fluorescently labeled conjugates. For example, streptavidin labeled with a fluorescent chelate can be used to bind to a biotinylated sample. The sample can then be detected via UV absorbance. This method can be used to detect the phosphorylation state of a protein that has been immunoprecipitated prior to being tagged at its phosphorylation sites. Used in this way, the phosphorylation state of a specific protein can be compared with a control sample without the need for protein sequencing, quantification or the use of antibodies selective for the phosphorylated protein itself.

The comparison methods disclosed herein can be also used for characterizing changes in the phosphorylation state of proteins in samples that have been treated with compounds such as nucleic acid sequences, proteins, protein fragments, and chemicals. Further, the methods are useful for detecting different phosphorylation states of proteins in "diseased" versus "normal" specimens. When used in this context, the methods provided herein can be used as diagnostic tools to identify subjects that are suffering from diseases caused by protein phosphorylation abnormalities.

Another aspect of the methods described herein provides reagents for mass spectrometric analysis of proteins. As set forth above, the general formula of the mass spectrometry reagents of the present invention is B-L-PhRG, where B is a binding agent that selectively binds to a capture reagent, L is a linker group that has at least one isotopically labeled isotope (i.e., $^2H$, $^{13}C$, $^{15}N$, $^{17}O$, $^{18}O$, or $^{34}S$) and contains at least one phosphorylation (phosphate) reactive group (PhRG) that selectively labels proteins at one or more residues that were formerly occupied by phosphate groups. Such mass spectrometry reagents preferably satisfy the formula:

where: B is a binding agent, PhRG is a protein reactive group, and The linker group should be "$B^1$—$X^1$ ... $B^2$" and not the entire molecule (that is not including "B" or "PhRG".

B—$B^1$—$X^1$—$(CH_2)_n$—$[X^2$—$(CH_2)m]_x$—$X^3$—$(CH_2)p$—$X^4$—$B^2$-PhRG is a linker group wherein: $X^1$, $X^2$, $X^3$ and $X^4$, and the $X^2$ and other $X^2$, are all independently selected from O, S, NH, NR, NRR'+, CO, COO, COS, S—S, SO, $SO_2$, CO-NR', CS-NR', Si-O, aryl or diaryl groups or $X^1$–$X^4$ may be absent; $B^1$ and $B^2$, are optional groups independently selected from COO, CO, CO-NR', CS-NR', $(CH_2)_q$-CONR', $(CH_2)_q$-CS-NR', or $(CH_2)_q$; n, m, p, q and x are whole numbers that can take values from 0 to about 100, where the sum of n+xm+p+q is less than about 100; R is an alkyl, alkenyl, alkynyl, alkoxy or an aryl group that is optionally substituted with one or more alkyl, alkenyl, alkynyl, or alkoxy groups; and R' is a hydrogen, an alkyl, alkenyl, alkynyl, alkoxy or an aryl group that is optionally substituted with one or more alkyl, alkenyl, alkynyl, or alkoxy groups, wherein one or more of the $CH_2$ groups in the linker can be optionally substituted with alkyl, alkenyl, alkoxy groups, an aryl group that is optionally substituted with one or more alkyl, alkenyl, alkynyl, or alkoxy groups, an acidic group, a basic group or a group carrying a permanent positive or negative charge; wherein one or more single bonds linking non-adjacent $CH_2$ groups in the linker can be replaced with a double or a triple bond and wherein one or more of the atoms in the linker can be substituted with a stable isotope.

These and other aspects of the invention will become evident upon reading the following detailed description.

SEQUENCE LISTING

The nucleic and amino acid sequences in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1 shows the amino acid sequence of a phosphorylated peptide.

DETAILED DESCRIPTION

In general, the invention provides reagents and methods for characterizing and/or comparing the phosphorylation states and levels of proteins.

More specifically, an aspect of the invention provides methods for removal of one or more phosphate groups from one or more amino acid residues in the protein, tagging the protein at such sites with a linker that contains at least one necessary isotope at the residues previously occupied by the phosphate group. At least one of the reactive groups in the linker targets the linker to the residue that was phosphorylated. A second reactive group can also be present in the linker and when it is present it preferably targets a binding agent. Both the first and second reactive groups may be the same. That is, if, e.g., ethandithiol is used as a linker, each of the thiol groups is considered a reactive group. The second reactive group may, alternatively, be selected for its ability to bind to a binding agent such as biotin, maltose, a hapten, an oligomeric histidine, and glutathione so that the bound protein may be easily isolated or substantially isolated from other components in a sample. After the protein is tagged it is then easily detectable using well-known chemical analysis methods, such as mass spectrometry.

The invention further provides methods for comparing phosphorylation states or levels of one or more proteins in one or more samples. The "comparison methods" involve providing a substantially chemically identical but differentially isotopically labeled protein reactive reagent for each sample, wherein the protein reactive reagent satisfies the formula:

where B is a binding agent that selectively binds to a capture reagent, L is a linker group having one or more atoms that is differentially labeled with one or more stable isotopes, and PhRG is a phosphate reactive group that selectively reacts with amino acid residues that were formerly phosphorylated. The comparison methods further include reacting each sample with one of the protein reactive reagents to provide proteins bound to the protein reactive reagent, whereby the bound proteins are differentially labeled with isotopes, e.g., stable isotopes. The bound proteins are then captured using a capture reagent that selectively binds B. The captured bound protein is preferably released from the capture reagent and detected using mass spectrometry. The proteins in the sample can also be subjected to enzymatic or chemical digestion prior to capture, using a capture reagent.

The methods and reagents described herein can be varied. For example, substitute reagents that have similar chemical properties to those described may be used. Further, the number and order of method steps described may be varied. For example, the phosphorylation site tagging reagent (i.e., the complex containing B-L-PhRG) used to tag the phosphorylated proteins can be "pre-synthesized" such that it contains a binding agent (B), a linker (L) and a phosphate reactive group (PhRG). Such a pre-synthesized tagging reagent allows tagging of a protein with a B-L-PhRG complex, selectively at sites formerly occupied by phosphate groups, in a single step.

The methods described herein may be practiced in multiple steps. For example, the protein(s) of interest may be initially denatured and reduced and the cysteinyl sulfhydryls can be chemically modified via alkylation or oxidation. In addition, O-linked carbohydrates can be removed by enzymatic cleavage using O-glycanase, for example, prior to phosphate removal. The protein, or sample containing one or more proteins, may then be reacted with a first reagent to remove phosphate groups from amino acid residues, thus leaving a unique reactive site the phosphate group formerly occupied. The unique reactive site may then be selectively tagged via subsequent reaction with a linker having at least two reactive groups. At least one of the two reactive groups is a phosphate reactive group PhRG. That is, at least one of the reactive groups is selective of the site formerly occupied by the phosphate group. The protein, with the attached linker is then reacted with a binding agent that attaches to a second reactive site on the linker. The end product of this multi-step tagging method is a protein that has, at the formerly phosphorylated amino acid residues, a B-L-PhRG complex.

Hence, end products of both the multi-step process and that of the single step process are the same. One of ordinary skill in the art will appreciate that alternative methods may be used to increase or decrease the number of steps. The end product, i.e., a protein that has been selectively labeled at phosphorylation sites, however, will be the same.

In the methods described herein the addition of reaction components may be independent or simultaneous. To facilitate discussion, however, methodologies are set forth, in the order in which the chemical reactions take place. Similarly, it will be understood by one of ordinary skill in the art that in many cases, 100% of the reactants may not be used to form the desired product. That is, in some cases, the product described or desired is just one of many products produced by the reaction.

I. Phosphate Reactive Group (PhRG)

A phosphate reactive group (PhRG) is a protein reactive group that selectively reacts with amino acid residues that were formerly phosphorylated. One function of the PhRG is to selectively target a linker to the site of phosphorylation on a protein. One method of facilitating the targeting ability of the PhRG is to remove the phosphate group from the protein and replace it with a different active group recognized by the PhRG (i.e., a group to which the PhRG is selective). In examples illustrated herein, phosphate groups are removed via hydroxide mediated β-elimination as shown below.

Hydroxide mediated β-elimination leaves dehydroalanine and □-methyl-dehydroalanine amino acid residues in place of the phosphoseryl (X=H) and phosphothreonyl (X=CH$_3$) residues, respectively. One of ordinary skill in the art will appreciate that any sufficiently strong base may be used to perform the elimination step. For example, methoxide, ethoxide, or any alkoxide may be used to facilitate the removal of the phosphate group. In addition, other ions, e.g., monovalent and divalent cations, can be used to selectively control the formation of PhRG addition and to minimize potential by products that may form during β-elimination.

A presynthesized PhRG may comprise any sufficiently strong nucleophile. More importantly, a PhRG preferably comprises a compound wherein the attacking nucleophile has sufficient selectivity and reactivity to participate in addition reactions with Michael-type substrates (activated alkenes). Preferably, the PhRG should not react with any other amino acids side chains or with the peptide backbone to any appreciable extent as to warrant its nonuse. For instance, the PhRG may comprise thiol.

Other useful PhRGs may be comprised of nitrogenous compounds including among others primary, secondary, and tertiary amines that have the formula RNH$_2$, RNHR', and RNR'R", respectively, where R, R', and R" can be C1 to C50 alkyl, for example, methylamine, ethylamine, propylamine, butylamine, isopropylamine, sec-butylamine, t-butylamine. In addition to C and H atoms, R, R', and R" of the amines can be comprised of O, S, and N atoms or other heteroatoms like halides (e.g., F atoms). Primary and secondary amides are also useful as PhRGs, wherein amides are compositions containing RCONH$_2$ or RCONHR', respectively, where R is H, or C1 to C50 alkyl, for example, formamide, acetamide, propionamide, n-butyramide, N-methylformamide, N-ethylformamide, N-methylacetamide, N-ethylacetamide, or where R and R' are joined to form a ring (lactams), for example butylrolactam. In addition to C and H atoms, the R and R' groups of the amides can also be comprised of O, S, and N atoms or other heteroatoms like halides (e.g., F atoms).

Additional PhRGs include imides having the formula RCONHCOR' where R is H or C1 to C50 alkyl, or aryl, R' is H or C1 to C50 alkyl, or aryl, or R and R' are joined to form a ring. Examples include phthalimide. In addition to C and H atoms, R and R' can be comprised of any combination of O, S, N atoms or other heteroatoms like halides (e.g., F atoms).

Hydroxylamines are also useful as PhRGs. Hydroxylamines have the formula NH$_2$ROH, where R is C1 to C50 alkyl, or aryl, for example ethanolamine. In addition to C and H atoms, R can be comprised of any combination of O, S, N atoms or other heteroatoms like halides (e.g., F atoms).

PhRGs can also be made from hydrazides which have the formula RCONHNH$_2$, where R is H or C1 to C50 alkyl, or aryl. In addition to C and H atoms, R can be comprised of any combination of O, S, N atoms or other heteroatoms like halides (e.g., F atoms).

Yet another type of PhRG which can be used in the disclosed methods are the hydrazines. Hydrazines have the formula HRNNR'H where R and R' are H or C1 to C50 alkyl, or aryl, for example, 1,2-diisobutyl hydrazine, 1,2-diisopropyl hydrazine. In addition to C and H atoms, R and R' can be comprised of any combination of O, S, N atoms or other heteroatoms like halides (e.g., F atoms).

Sulfites (SO$_3$), for example sodium sulfite, and sulfinates having the formula RSO$_2$ can also be used as PhRGs, where R is C1 to C50 alkyl, or aryl, for example methanesulfinate and benzenesulfinate. In addition to C and H atoms, R can be comprised of any combination of O, S, N atoms or other heteroatoms like halides (e.g., F atoms).

Sulfonamides having the formula RSO$_2$NH$_2$, where R is C1 to C50 alkyl, or aryl, for example methanesulfonamide, ethanesulfonamide, and phenylsulfonamide are useful PhRGs. In addition to C and H atoms, the R group in sulfonamides can be comprised of any combination of O, S, N atoms or other heteroatoms like halides (e.g., F atoms).

II. Linker Groups

A linker group (L) provides a backbone to connect the protein to the binding agent and acts to "tag" the protein. The linker group also provides a location for inclusion of differentiating isotopes or moieties (also to "tag" the protein). For example, a linker group of the invention may include heavy isotopes such as $^2$H, $^{13}$C, $^{15}$N, $^{17}$O, $^{18}$O, or $^{34}$S.

In the illustration provided below the linker group has two reactive groups (i.e. two thiol groups), one of which functions as the PhRG. The linker group can be added via Michael addition to the protein after the β-elimination step, as shown below. If the binding agent B is already attached to the linker and the PhRG (in this illustration B-CH$_2$CH$_2$-SH) the attachment of the B-L-PhRG could be performed in a single step.

As discussed above, when the protein is being tagged using a multistep reaction (i.e., when a presynthesized B-L-PhRG is not being used) the linker group preferably includes at least two reactive groups. The first reactive group (i.e., the thiol in the above illustration) targets the linker to the site formerly occupied by the phosphate group, and the second reactive group connects the linker to the binding agent (B) as shown below.

The linker group is preferably soluble in the liquid sample to be analyzed. Additionally, a preferred linker group is chemically stable, e.g., the linker group preferably comprises a compound that is substantially chemically "inert" to components of the sample (other than the protein) as well as to the binding agent. That is, the linker group, when bound to B, preferably does not interfere with the specific interaction of the B with the capture reagent (CR) or interfere with the displacement of the B from the CR by a displacing ligand or by a change in temperature or solvent.

The linker group preferably binds minimally or not at all to other components in the system, to the reaction vessel surfaces or to the CR. Any non-specific interactions of the linker group are preferably broken after multiple washes that leave the B-CR complex intact. Linker groups preferably do not undergo peptide-like fragmentation during mass spectrometry analysis. At least some atoms of a linker group are preferably readily replaceable with stable heavy-atom isotopes.

Further, the linker group preferably contains groups or moieties that facilitate ionization of binding reagents, peptides, substrates or reaction products. To promote ionization, the linker group may for example contain acidic or basic groups, e.g., COOH, $SO_3H$, primary, secondary or tertiary amino groups, nitrogen-heterocycles, ethers, or combinations of such groups. The linker may also contain groups having a permanent charge, e.g., phosphonium groups, quaternary ammonium groups, sulfonium groups, chelated metal ions, tetralky or tetraryl borate or stable carbanions. The covalent bond of the linker group to B or PhRG preferably is not unintentionally cleavable by chemical or enzymatic reactions during assay. In some cases it may be desirable to cleave the linker group from the B or from the PhRG, for example to facilitate release from an affinity column. Thus, the linker group may be cleavable, for example, by chemical, thermal or photochemical reaction. Photocleavable groups in the linker may include, e.g., an 1-(2-nitrophenyl)-ethyl group. Thermally labile linker groups may comprise, for example, a double-stranded duplex formed from two complementary strands of nucleic acid, a strand of a nucleic acid with a complementary strand of a peptide nucleic acid, or two complementary peptide nucleic acid strands which will dissociate upon heating. Cleavable linkers also may comprise compounds having disulfide bonds, acid or base labile groups, including among others, diarylmethyl or trimethylarylmethyl groups, silyl ethers, carbamates, oxyesters, thioesters, thionoesters, thiocarbamates, and α-fluorinated amides and esters. Enzymatically cleavable linkers may include for example, protease-sensitive amides or esters, P-lactamase-sensitive P-lactam analogs and linkers that are nuclease-cleavable, or glycosidase-cleavable.

Linker groups may vary in length to facilitate generation of B-L-PhRG complexes that may vary in mass. Methods of generating various linkers are discussed in WO 00/11208 to Aebersold et al., which is herein incorporated by reference.

III. Enrichment

An enrichment process may be used to facilitate the methods of the invention by enhancing interaction between the binding agent (B) and a capture reagent (CR). The attachment to a capture reagent allows proteins or peptides (protein fragments) that have been tagged with B-L-PhRG to be isolated or substantially isolated from other molecules (such as non-phosphorylated proteins) that failed to react with the B-L-PhRG complex. In general, a binding agent binds to a capture reagent and "non-tagged" molecules are then washed away with buffers and other solutions (e.g., successes washes of 10 column volumes of 2×PBS, PBS, 100 mM $NH_4HCO_3$, and 20% methanol). The B-L-PhRG may then be appropriately released from the CR and subjected to further analysis.

A. Binding Agents and Capture Reagents

Suitable binding agents (B) preferably bind selectively either covalently or non-covalently and with high affinity to a capture reagent (CR). A CR binds to the binding agent and allows other components in the sample to be washed away from the bound protein. The CR-B interaction or bond preferably remains intact after extensive and/or multiple washings with a variety of solutions to remove non-specifically bound components. Preferably, neither CR or B react chemically with other components in the assay system and both groups should be chemically stable over the time period of an assay or experiment. The binding agent preferably does not undergo peptide-like fragmentation during mass spectrometric analysis. The binding agent is preferably soluble in the liquid sample to be analyzed and the CR preferably remains soluble in the sample even though attached to an insoluble resin such as avidin agarose. As used herein, soluble means that the CR is sufficiently hydrated or otherwise solvated such that it functions to bind to B. CR or CR-containing conjugates preferably are not present in the sample to be analyzed, except when added to capture B.

Examples of suitable B and CR pairs for practicing the invention include:

d-biotin or structurally modified biotin-based reagents, including d-iminobiotin, that bind to proteins of the avidin/streptavidin, and that may, for example, be used in the forms of strepavidin-Agarose, oligomeric-avidin-Agarose, or monomeric-avidin-Agarose; any 1,2-diol, such as 1,2-dihydroxyethane ($HO-CH_2-CH_2-$ OH). Further included are other 1,2-dihydroxyalkanes including those of cyclic alkanes, e.g., 1,2-dihydroxycyclohexane which bind to an alkyl or aryl boronic acid or boronic acid esters, such as phenyl-B (OH), or hexyl-B(OEthyl), that may be attached via the alkyl or aryl group to a solid support material, such as Agarose; in short, any immobilized form of avidin or streptavidin.

maltose that binds to maltose-binding protein (as well as any other sugar/sugar binding protein pair or more generally to any ligand—ligand binding protein pairs that has properties discussed above);

a hapten, such as dinitrophenyl group, or any antibody where the hapten binds to an anti-hapten antibody that recognizes the hapten, for example dinitrophenyl group will bind to an anti-dinitrophenyl-lgG;

a ligand that binds to a transition metal. For example, an oligomeric histidine will bind to Ni(II), the transition metal CR may be used in the form of a resin bound chelated transition metal, such as nitrilotriacetic acid-chelated Ni(II) or iminodiacetic acid-chelatedNi(II);

glutathione that binds to glutathione-S-transferase.

In general, any B-CR pair commonly used for affinity enrichment that meets the suitability criteria discussed above may be used to practice the invention. Biotin and biotin-based binding agents are preferred. Of particular interest are structurally modified biotins, such as d-iminobiotin, that elute from avidin or strepavidin columns under solvent conditions compatible with ESI-MS analysis, such as dilute acids containing 10–40% organic solvent. It is expected that d-iminobiotin tagged compounds will elute in solvents below a pH of about 4. d-iminobiotin tagged protein reactive reagents may be synthesized by methods described herein for the corresponding biotin tagged reagents.

B. Displacement Ligand

A displacement ligand (DL) is optionally used to displace B from CR. A suitable DL is preferably chemically and enzymatically stable in the sample to be analyzed and preferably does not react with or bind to components (other than CR) in samples or bind non-specifically to reaction vessel walls. Suitable DLs preferably do not undergo peptide-like fragmentation during mass spectrometry analysis, and its presence in samples preferably does not significantly suppress the ionization of a tagged peptide, substrate or reaction product conjugates.

DL itself preferably is minimally ionized during mass spectrometric analysis and the formation of ions composed of DL clusters is preferably minimal. The selection of a suitable DL depends upon the B and CR groups that are employed. In general, a DL is selected to displace B from CR in a reasonable time scale, preferably within a week of its addition, but more preferably within a few minutes or up to an hour. The affinity of a DL for a CR is preferably comparable to or stronger than the affinity of the tagged compounds containing B, for the CR. Furthermore, a DL is preferably soluble in solvent used during elution of tagged compounds containing B. DL may comprise a derivative or structural modification of a selected B. Examples of suitable DLs include d-biotin or d-biotin derivatives, particularly those containing groups that suppress cluster formation or do not suppress ionization during mass spectrometric analysis.

IV. Exemplary Uses

A. Characterization of the Phosphorylation State of Multiple Proteins

The methods and reagents described herein may be used to profile the phosphorylation states of multiple proteins. The proteins may be derived from tissue samples such as tumor samples, body fluids such as urine, saliva, or blood, or cell cultures. Using the present methods to tag proteins, samples containing a heterologous mixture of proteins may be exposed to one or more differentially labeled B-L-PhRG complexes, be substantially isolated, and then subjected to detection based upon the differences in their length and/or weight. Such analysis provides a profile of the phosphorylation states of the proteins from the biological sample.

B. Diagnostic for the Detection of Diseases Associated with Hyper- or Hypo-Phosphorylation of Proteins As mentioned above, several disease states have been correlated with the abnormal phosphorylation of proteins. Abnormal in this context refers to a deviation from normal characteristics. Normal characteristics can be found in a control, a standard for a population, etc. For instance, when the abnormal condition is a diseased condition, such as phosphorylation of the tau protein in Alzheimer's disease, an appropriate source of "normal characteristics" might include an individual or a population standard of individuals believed not to be suffering from the disease.

Likewise, abnormal may refer to a condition that is associated with a disease. The term "associated with" includes, for example, an increased risk of developing the disease as well as the disease itself. For instance, a certain abnormality (such as a hyperphosphorylation of tau protein) can be described as being associated with the biological condition of Alzheimer's disease (decrease in bone mass); thus, the abnormality is predictive both of an increased risk of developing Alzheimer's disease and of the presence of Alzheimer's disease.

Abnormal protein modification, such as abnormal protein phosphorylation, refers to the modification of a protein that is in some manner different from expression of the protein in a normal situation. This includes but is not limited to: (1) a mutation in the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of an increased amount of the phosphorylated protein, compared to a control or standard amount; (5) expression of an decreased amount of the phosphorylated protein, compared to a control or standard amount; (6) alteration of the subcellular localization or targeting of the protein; (7) alteration of the temporally regulated expression of the protein (such that the protein is expressed when it normally would not be, or alternatively is not expressed when it normally would be); and (8) alteration of the localized (e.g., organ or tissue specific) expression of the protein (such that the protein is not expressed where it would normally be expressed or is expressed where it normally would not be expressed), each compared to a control or standard.

Controls or standards appropriate for comparison to a sample for the determination of abnormality include laboratory values, keeping in mind that such values may vary from laboratory to laboratory. Laboratory standards and values may be set based on a known or determined population value and may be supplied in the format of a graph or table that permits easy comparison of measured, experimentally determined values.

Determining that a protein or a set of proteins are displaying an abnormal phosphorylation state can be accomplished using the present invention methods. Specifically, a sample containing the test protein(s) (i.e., proteins that are from a source that is suspected of displaying abnormal phosphorylation levels) is contacted with a B-L-PhRG complex, and in a separate reaction, contacting a control sample with a differentially labeled B-L-PhRG complex. The samples can then be analyzed to determine if the test sample contains either hyper- or hypo- phosphorylated proteins compared to the control.

C. Screening to Identify Compounds that affect the Phosphorylation State of Proteins The methods described herein can also be used to identify potential therapeutic agents, such as chemical agents, therapeutic nucleic acid molecules, or peptides, that act to alter the phosphorylation state of proteins suspected of contributing to disease. Once an abnormally phosphorylated protein has been identified as contributing to a disease state the methods described herein can be used to screen for compounds that alter the phosphorylation state of the protein. This can be accomplished by contacting a sample, i.e., a sample from a subject, cell culture, or tissue culture that displays the hyper- or hypo- phosphorylated protein to the test compound (i.e., therapeutic). The proteins from the sample can then be isolated and tagged with the B-L-PhRG complex and analyzed to see if the test compound was capable of altering the phosphorylation state of the protein.

The amount or concentration of the therapeutic may need to be varied in order to determine whether it effectively alters the phosphorylation level (state) of the protein. One of ordinary skill in the art will appreciate what amounts would be necessary or that simple experiments using varying concentrations of the therapeutic can be designed. For example, using concentrates of the therapeutic ranging from about 1 pg/mL to about 1 µg/mL, or about 1 ng/mL to about 1 g/mL identifies the concentration at which the therapeutic compound alters the phosphorylation state of the protein.

VI. Experimental Designs

Internal standards, which are appropriately isotopically labeled, may be employed in the methods of this invention to measure absolute quantitative amounts of proteins in samples. Internal standards for use in methods herein to quantify one or several proteins in a sample are prepared by reaction of affinity labeled protein reactive reagents with a known protein to generate a bound standard. Bound standards are substantially chemically identical to the corresponding peptides generated from digestion of test proteins, except that they are differentially isotopically labeled to allow their independent detection by MS techniques.

The methods of this invention can also be applied to determine the relative quantities of one or more proteins in two or more protein samples. Specifically, the proteins in each sample are reacted with B-L-PhRG complexes that are substantially chemically identical but differentially isotopically labeled. The samples are combined and processed as one. The relative quantity of each tagged peptide reflects the relative quantity of the protein from which the peptide originated. This quantity is determined by the measurement of the respective isotope peaks by mass spectrometry. The methods of this invention can be applied to the analysis or comparison of multiple samples. Samples that can be analyzed by methods of this invention include, e.g., cell homogenates; cell fractions; biological fluids including urine, blood, and cerebrospinal fluid; tissue homogenates; tears; feces; saliva; lavage fluids such as lung or peritoneal lavages; mixtures of biological molecules including proteins, lipids, carbohydrates and nucleic acids generated by partial or complete fractionation of cell or tissue homogenates. The methods of this invention employ mass spectrometry (MS) and MS methods known to those persons skilled in the art. While a variety of MS analysis methods may be used to practice the methods herein, Matrix Assisted Laser Desorption Ionization MS (MALDI-MS) and Electrospray Ionization MS (ESI-MS) methods have shown to be particularly useful.

Proteins or peptides (fragments of full-length proteins) that have been tagged with the B-L-PhRG can be analyzed using LC-MS$^2$, CE-MS$^2$ with data dependent fragmentation or other suitable means. Methods and instrument control protocols are well-known in the art and are described, for example, in Ducret et al., *Prot Sci.* 7:706–719, 1998; Figeys and Aebersold, Electrophoresis 19:855–892,1998; Figeys et al. *Nature Biotec.* 14:1579:1583,1996; or Haynes et al., *Electrophoresis* 19:939–945,1998.

Both the quantity and sequence identity of the proteins from which the tagged peptides originate can be determined by automated multistage MS. This is achieved by the operation of the mass spectrometer in a dual mode in which it alternates in successive scans between measuring the relative quantities of eluting peptides and recording the sequence information of selected peptides. Peptides are quantified by measuring in the MS mode the relative signal intensities for pairs of peptide ions of identical sequence that are tagged with the isotopically light or heavy forms of the reagent, respectively, and which therefore differ in mass by the mass differential encoded within the binding agent. Peptide sequence information is automatically generated by selecting peptide ions of a particular mass-to-charge (m/z) ratio for collision-induced dissociation (CID) in the mass spectrometer operating in the MS$^2$ mode. (Link, A. J. et al. *Electrophoresis* 18:1314–1334, 1997, Gygi, S. P. et al. Electrophoresis 20:310–319,1999, and Gygi, S. P. et al. *Mol Cell. Biol.* 19:1720–1730,1999). The resulting CID spectra are then automatically correlated with sequence databases to identify the protein from which the sequenced peptide originated. Combination of the results generated by mass spectrometry and mass spectrometry analyses of proteins or peptides tagged with a B-L-PhRG and differentially labeled samples therefore determines the relative quantities as well as the sequence identities of the components of protein mixtures in a single, automated operation.

In some instances the use of mass spectrometry analyses might not be desirable. In these instances the spectrophotometric qualities and binding properties of biotin can be exploited. For example, the biotin labeling procedure can be used in conjuction with ultraviolet (UV) spectroscopy to measure the incorporation of biotin which absorbs at 220 nm (Przyjazny A. et al. *Anal. Chem.* 62:2536–2540,1990). Such UV detection could be used on a single protein system to evaluate the extent of seryl and/or threonyl phosphorylation of this protein when the cell or organism is subjected to some external perturbation. The single protein could be immunopreciptiated or isolated from a gel prior to be derivitized.

Fluorescence detection is also feasible since many studies have used streptavidin labeled with a fluorescent chelate to detect the biotinylated tag (Luo LY, and Diamandis EP, *Luminescence* 15:409–413, 2000; and Harma H et al. *Luminescence* 15:351–355, 2000). In this application the derivatized proteins would be non-covalently bound by the fluorescent streptavidin conjugate. Detection of the tagged proteins would then be monitored by fluorescence spectroscopy and quantified by the signal intensity.

SPECIFIC EXAMPLES

1. Sample Preparation.

Figure 1:
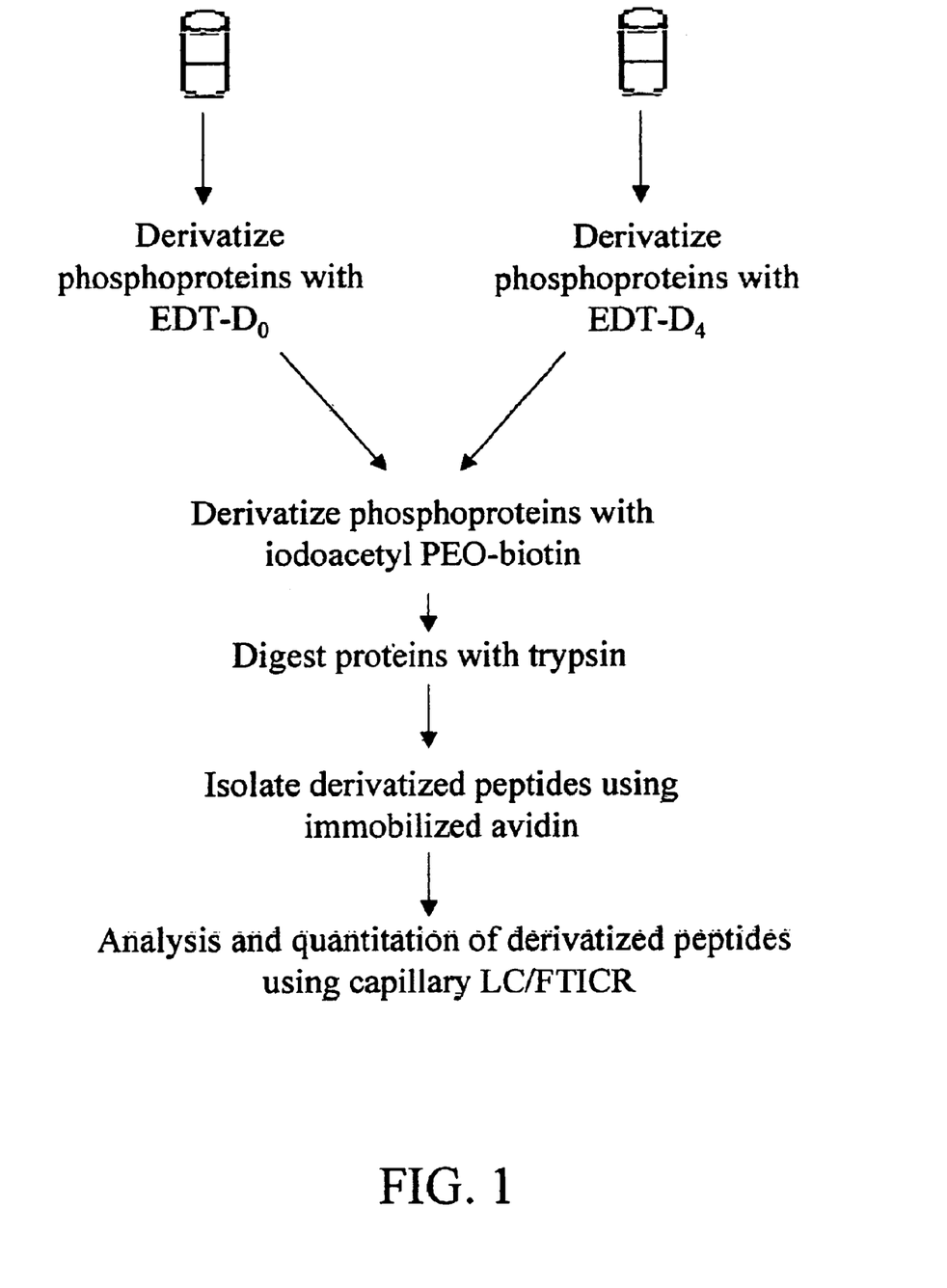
FIG. 1 shows a general scheme for selective labeling or tagging of phosphorylated proteins at the sites of phosphorylation.
Figure 2:
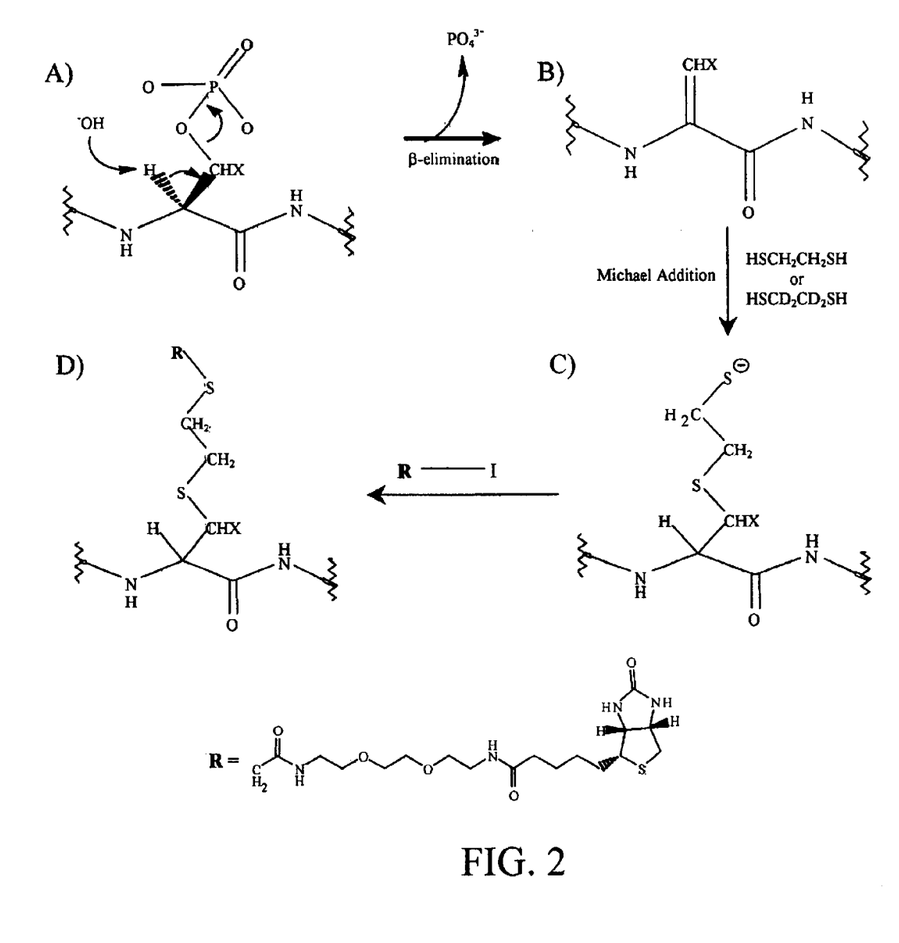
FIG. 2 shows a reaction scheme including the derivatization of the phosphoserine (X=H) or phosphothreonine (X=$CH_3$) residues of proteins to ultimately produce biotinylated peptides that can be affinity isolated from non-phosphorylated peptides via avidin affinity chromatography.

The overall modification and isolation of phosphopeptides using the methods described herein is shown in FIG. 1. Although initial experiments were conducted using the two step labeling process, the use of a single reagent (B-L-PhRG) to perform a one step labeling is preferred. Briefly, two identical samples of β-casein, or protein extracts obtained from whole cell lysates or tissue samples were prepared as follows. A quantity of protein (between about 100 pg to 1 mg) was denatured in about 6 M guanidine hydrochloride (GdnHCl) in a volume between about 1.0 and 1.5 ml. Disulfide bonds were reduced by adding about a 5 molar excess of tris(2-carboxyethyl)phosphine hydrochloride (TCEP·HCl) over cysteinyl residues (assuming 1 mg of protein is equivalent to 30 nmol of protein and that there are 6 cysteinyl residues per protein molecule) and incubating the sample for about 1 h at about 370C. Additionally, due to the reactivity of 0-linked carbohydrates under the β-elimination conditions, they can be removed by enzymatic cleavage using O-glycanase (Glko, Inc. Novato Calif.), for example, prior to p-elimination of the phosphate moieties. The exposed cysteinyl residues were blocked using either reductive alkylation (Gurd, F. R. N. *Methods in Enzymology*, Hirs, C. H. W., ed.; Academic Press, Inc. New York, 1967, Vol. 11, pp 532–541) or performic acid oxidation (Hirs, C. H. W. *Methods in Enzymology*, Hirs, C.H.W., ed.; Academic Press, Inc. New York, 1967, Vol. 11, pp 197–199). After removal of the excess reagents using either gel filtration, diafiltration, or dialysis, the phosphate groups present on phosphoserine and phosphothreonine residues were removed via hydroxide ion mediated β-elimination (FIGS. 2A and 2B).

The formation of the α, β-unsaturated double bond produced an electrophilic center at the β position of the formerly phosphorylated residues. This reactive β-carbon center (FIG. 2B) was then modified by the addition of ethanedithiol ($HSCH_2CH_2SH$ or EDT) via Michael addition to produce a new molecule containing a covalent thioether linkage (FIG. 2C).

The reaction conditions for β-elimination and EDT labeling are based upon previously published methods describing the β-elimination of phosphate with subsequent Michael addition of various sulfhydryl nucleophiles. (Meyer, et al., *FEBS Lett* 204:61–6, 1986; Mega, et al., *J. Biochem* (Tokyo) 100:1109–16, 1986; Fadden, et al., *Anal Biochem* 225: 81–88, 1995; and Jaffe and Pant *Biochemistry* 37: 16211–16224, 1998). The reaction conditions, however, were modified to facilitate differential labeling of a complex protein mixture or proteome. Since this described method was initially applied to a protein (β-casein) sample containing only phosphoseryl residues, the conditions may have to be modified to accommodate the labeling of phosphothreonyl residues. For example, the reaction time may have to be increased to several hours or the addition of monovalent and divalent cations may need to be added to facilitate labeling. This may also be the case when labeling with the single molecule B-L-PhRG.

More specifically, the protein sample was divided into two equal aliquots and labeled with EDT-$D_0$($HSCH_2CH_2SH$) or EDT-$D_4$ ($HSCD_2CD_2SH$), respectively. The β-elimination/EDT reaction mixture consisted of the following components: about 150 μl of $H_2O$, about 185 μl of dimethyl sulfoxide, about 35 μl of ethanol, about 35 μl of acetonitrile, about 5 μl of about 250 mM EDTA (pH 8.0), about 45 μl of 5 M NaOH, and 11 μl of either EDT-$D_0$ or EDT-$D_4$. All solvents (except for EDT) were degassed with $N_2$ for about 5 minutes before and after preparation of the reaction mixture just prior to EDT addition. After EDT addition, about 200 μl of the β-elimination/EDT reaction mixture was added to the lyophilized protein sample (a maximum of about 1 mg of deglycosylated, cysteinyl blocked protein per about 200 μl of the β-elimination/EDT reaction mixture). The samples were incubated for about 1 hr at about 55° C. under a $N_2$ atmosphere, cooled to room temperature, and the reaction quenched by neutralizing with acetic acid.

After quenching the reaction, the protein samples labeled with EDT-$D_0$ or EDT-$D_4$ were combined and desalted using gel filtration equilibrated with about 0.1 M $NH_4HCO_3$, a pH of about 8.2. The EDT-labeled proteins (volume of 1 about ml) were denatured by adding solid GdnHCl to achieve about 6 M, and reduced with TCEP·HCl as described above. The sulfhydryl content was determined by the 5,5'-dithiobis (2-nitrobenzoic acid) (DTNB) assay (Ellman, G. L. Arch Biochem Biophys 82:70, 1959), or estimated based on the concentration of protein present as determined by the BCA assay (Pierce, Rockford Ill.). The EDT-labeled residues were biotinylated by adding a 5 molar excess of (+)-biotinyl-iodoacetamidyl-3,6-dioxaoctanediamine (iodoacetyl-PEO-biotin) (Pierce, Rockford, Ill.). The biotinylation reaction was allowed to proceed with constant stirring in the dark for 90 min at ambient temperature. The EDT-acetyl-PEO-biotin labeled proteins were desalted into about 0.1 M $NH_4HCO_3$, pH of about 8.2, and digested overnight at about 37° C. with modified trypsin (Promega, Madison, Wis.) using about a 1:50 (w:w) trypsin-to-protein ratio. Tryptic activity was quenched by boiling the sample followed by the addition of phenylmethylsulfonylfluoride to a final concentration of about 1 mM.

The labeled peptides were purified by affinity chromatography using ImmunoPure® immobilized monomeric avidin from Pierce (Rockford, Ill.) as follows. Between about 1.2 ml and about 1.5 ml of avidin slurry was packed in a glass pasture pipefte containing a glass wool plug. Prior to sample loading, irreversible biotin binding sites were blocked as per manufacturer's instructions. The sample containing the B-L-PhRG labeled peptides was added to the column and permitted to incubate for about 30 min at ambient temperature. The column was washed with about 15 ml of 2× PBS, 15 ml of 1× PBS, and about 15 ml of 0.1 M $NH_4HCO_3$, pH 8.2. The labeled peptides were eluted using about 2 ml of 30% acetonitrile/0.4% TFA. The recovery of labeled peptides was quantified using the BCA assay.

2. Analysis of Biotinylated Phosphopeptides.

Figure 3A:
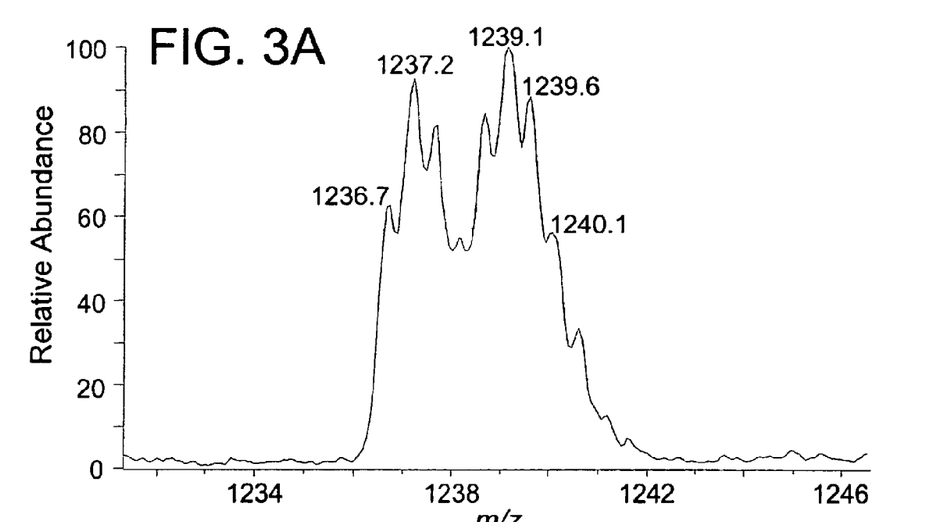
FIGS. 3A and 3B show mass spectra for the B-L-PhRG labeled phosphorylated peptide FQSPEEQQQTEDELQDK (SEQ ID NO: 1) where the phosphoseryl residue (SP) has been modified with B-L-PhRG-D$_0$ or B-L-PhRG-D$_4$.
Figure 3B:
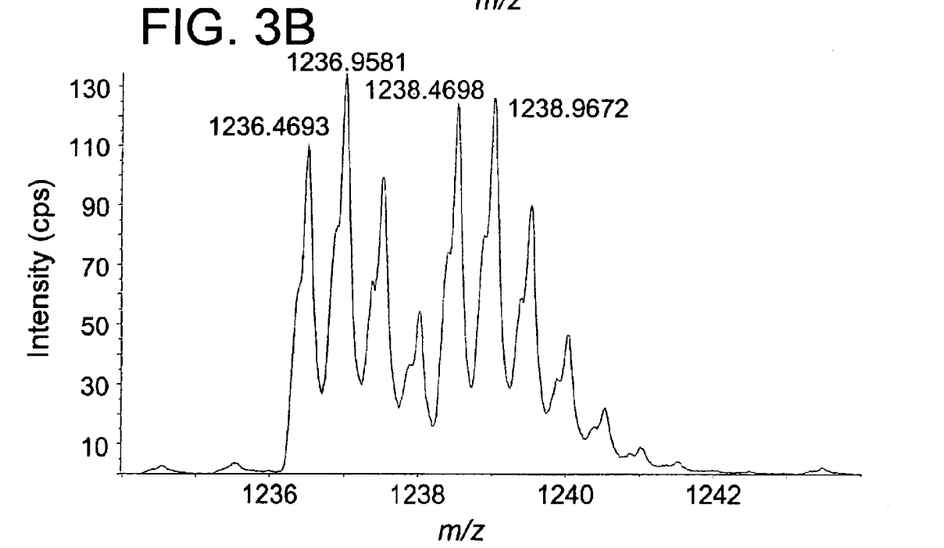

The enriched mixture of biotinylated phosphopeptides was analyzed by capillary reversed-phase liquid chromatography-mass spectrometry. Peaks corresponding to the mass of the derivatized phosphopeptides predicted from the sequence of β-casein were identified. In all cases, pairs of peaks were detected with the differences in their masses being equivalent to the mass difference of the light (B-L-PhRG-$D_0$) and heavy (B-L-PhRG-$D_4$) isotopic versions of the B-L-PhRG label. The ratio of the isotopically distinct pairs of peptides was 1:1, demonstrating the effectiveness of the labeling scheme to provide correct quantitative results. The spectra for the B-L-PhRG labeled phosphorylated peptide FQS$^P$EEQQQTEDELQDK (SEQ ID NO: 1) where the phosphoseryl residue has been modified with B-L-PhRG-$D_0$ or B-L-PhRG-$D_4$ are shown in FIG. 3. In addition to the peptide mass, data dependent MS/MS in conjunction with automated database searching was used to (1) identify the peptide as a tryptic fragment of β-casein and (2) identify serine as the site of the B-L-PhRG-$D_0$ and B-L-PhRG-$D_4$ modification, and hence, phosphorylation.

3. Creation of a Presynthesized Phosphate Tagging (PhR) Reagent

All solvents and solutions (except for ethanedithiol (EDT)) were degassed with $N_2$ for 5 minutes. A solution of 0.1 M TCEP·HCl in 0.2 M Tris, pH 8.4 was prepared and the pH of this reducing solution adjusted to 8.3 using 5 M NaOH. The reaction solution was made by combining the following reagents to a glass sample vial containing a stirring bar: 250 μl of 0.1 M TCEP·HCl in 0.2 M Tris (pH 8.3), 25 μl of 250 mM EDTA (pH 8.0), 225 μl of ethanol, and 400 μl of 2% EDT-$D_0$ in ethanol (a 5 molar excess over the amount of iodoacetyl-PEO-biotin that was used). After mixing, 5 mg of iodoacetyl-PEO-biotin was added, followed by an additional 250 μl of the reducing solution.

Once the iodoacetyl-PEO-biotin was thoroughly dissolved, the headspace in the reaction vessel was exposed to $N_2$ for several seconds and sealed with a silicon/Teflon septum. The reaction was permitted to proceed with constant stirring in the dark for 2.5 h at ambient temperature, and was quenched by neutralizing with 80 μl of 10% acetic acid. To completely quench the reaction the apparent pH of the solution should be 6.0. A volume of 600 μl of $H_2O$ was then added prior to ether extraction. Excess EDT and any potential disulfide linked EDT byproducts were removed by extracting 2 times with equal volumes of water-saturated diethyl ether containing 30% ethanol.

Residual diethyl ether was removed over a stream of $N_2$. Isolation of the B-L-PhRG reagent (EDT-$D_0$-acetyl-PEO-biotin, i.e., the B-L-PhRG-$D_0$ version) was performed by affinity chromatography using immobilized avidin. The eluant (B-L-PhRG) was lyophilized and stored at −20° C. The reaction products were analyzed by direct infusion of 0.01 μg/μl of the reaction mixture into the electrospray interface of a PE Sciex API QStar Pulsar hybrid quadrupole-TOF mass spectrometer (PE Sciex Instruments, Toronto, Canada) using water/methanol (1:1, v:v) with 1% acetic acid as the solvent.

Figure 4:
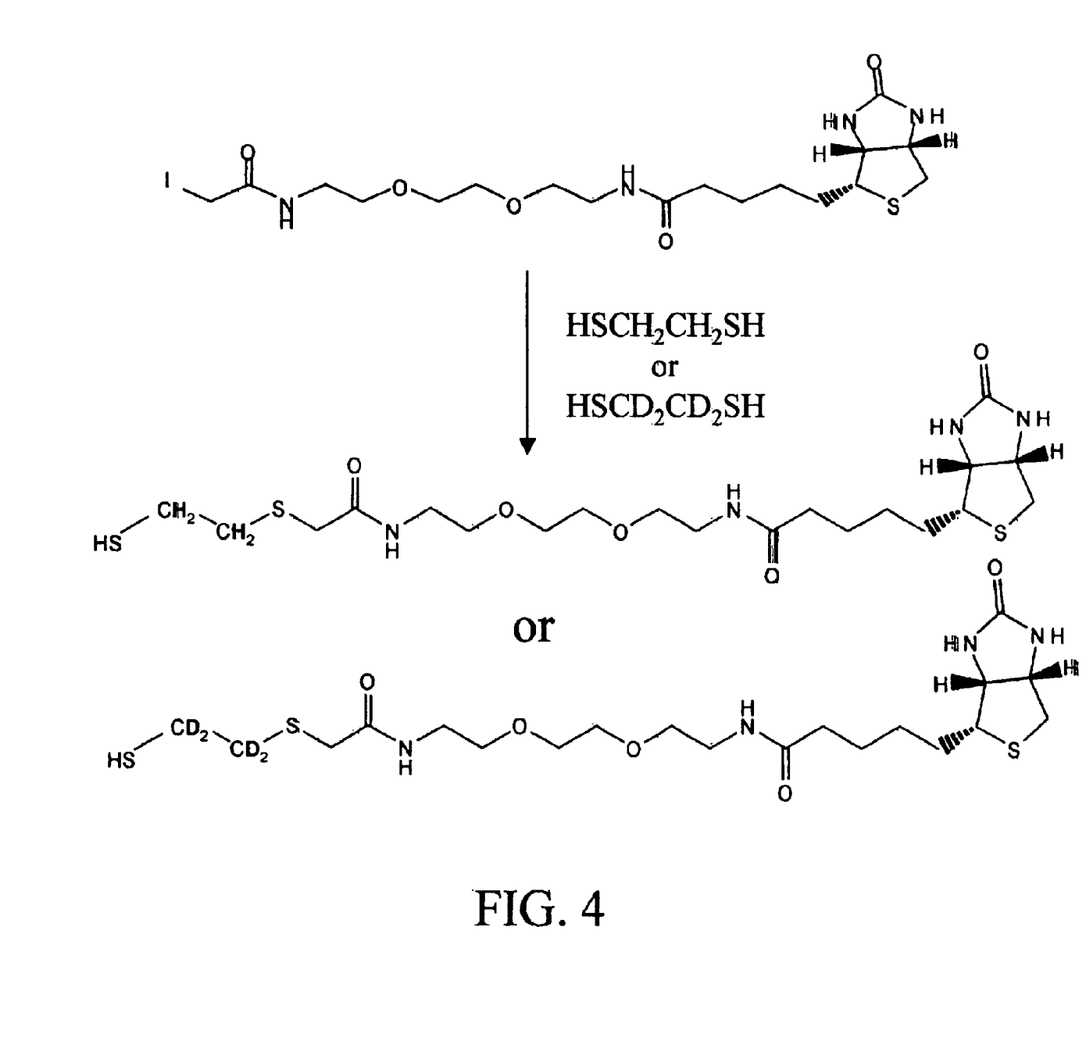
FIG. 4 shows a scheme for formation of a phosphate reactive group (B-L-PhRG) complex. The complex incorporates a light or heavy isotopic linker (in the illustration either ethanedithiol light or heavy) onto iodoacetyl PEO-biotin for use in a one-step Michael addition of the B-L-PhRG to phosphopeptides.
Figure 5:
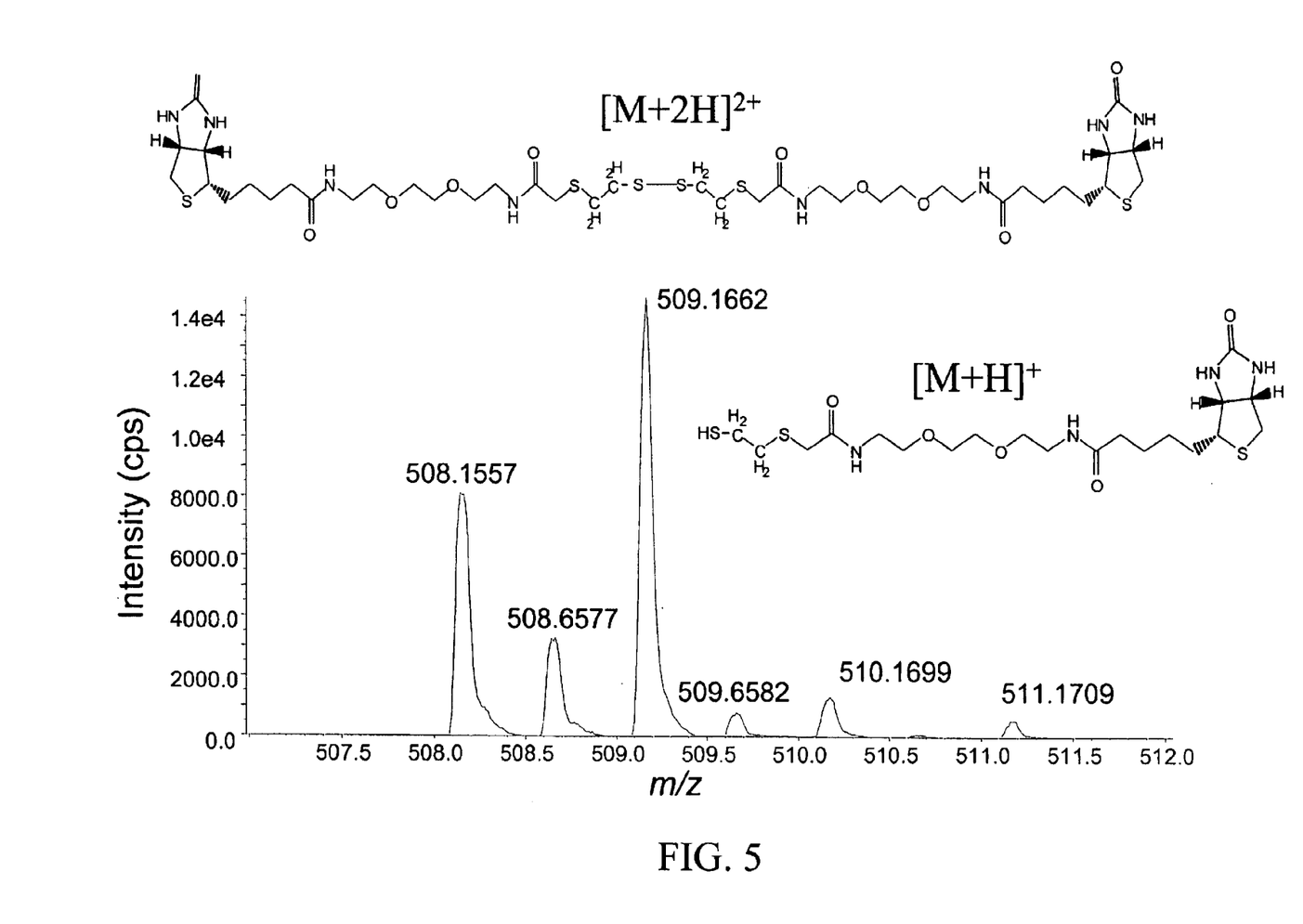
FIG. 5 shows a graph of the mass spectrum analysis of products formed during the synthesis of a B-L-PhRG complex.

The resulting B-L-PhRG was analyzed using ESI mass spectrometry. Results of the analysis are shown in FIG. 4. In the region of the expected mass of the B-L-PhRG reagent, two major components are observed. One of these components (m/z 509.1662) is a singly charged species and corresponds to the B-L-PhRG reagent containing the free sulfhydryl group, the linker region, and the biotin moiety. The second component (m/z 508.1557) is a doubly charged species in which a disulfide bond between two B-L-PhRG molecules has formed. The singly charged species of this component was also detected at m/z 1015.3114. The demonstrated ability to synthesize the B-L-PhRG molecule represents the first step towards the use of a single reagent to derivatize phosphorylated proteins. Depending on the nature of the B-L-PhRG molecule, the treatment to remove the phosphate groups from the proteins can be performed initially, followed by isolation of the proteins and subsequent attachment of the B-L-PhRG label to the chemically dephosphorylated residues.

In addition to the above-described presynthesized B-L-PhRG complex, several other complexes containing both a binding group and a linker are commercially available. Because these complexes generally contain a binding group and a linker, the linker does not need to have two reactive groups. The linker in these complexes may only have a PhRG. Examples of such commercially available B-L complexes are Sulfo-NHS-LC-Biotin, Sulfo-NHS-LC—LC-Biotin, Sulfo-NHS-Biotin, Sulfo-NHS-SS-Biotin, Sulfo-LC-Biotin, Sulfo-LC-LC-Biotin, NHS-Biotin, NHS-Iminobiotin, PFP-Biotin, NHS-PC-LC-Biotin, PEO-Maleimide Activated Biotin, Biotin-BMCC, PEO-Iodoacetyl Biotin, Iodoacetyl-LC Biotin, Biotin-HPDP, Biotin PEO-Amine, Biotin PEO-LC-Amine, 5-(Biotinamido)pentylamine, Biocytin Hydrazide, Biotin Hydrazide, Biocytin-LC-Hydrazide, Psoralen-PEO-Biotin, PEO-Biotin Dimer, Photoactivatable Biotin, Biotin-LC-ASA, Biocytin, Biotin DPPE, Biotin-LC-DPPE, Sulfo-SBED, all of which are available from Pierce, Rockford Ill.

4. Detecting Tyrosine Phosphorylation

Methods for targeting only phosphorylated tyrosyl residues with a suitable PhRG (either nucleophilic or electrophilic) can be performed using three methods as outlined in FIG. 6 (Methods 1, 2, and 3) and discussed below. These methods are also provided in Haystead et al. (U.S. Pat. No. 5,686,310, which is herein incorporated by reference). Depending upon the selected PhRG, in addition to B and L, a constructed B-L-PhRG molecule can be (1) used to label phosphoseryl and phosphothreonyl residues (using β-elimination/Michael addition) and phosphotyrosyl residues (using Method 1) or (2) altered to create two different B-L-PhRG labels, one specific for phosphoseryl and phosphothreonyl residues (using β-elimination/Michael addition) and the other for only phosphotyrosyl residues (using Method 2 or 3). In conjunction with varying reaction conditions, the incorporation of suitable and different isotopically labeled linkers, and/or different binding agents or PhRGs into the B-L-PhRG molecule, the ability to simultaneously quantitate the extent of serine, threonine, and tyrosine phosphorylation is possible. For example, this selective labeling would facilitate the assignment of the B-L-PhRG to the appropriate residue (serine, threonine, or tyrosine) of the peptide analyzed by LC/MS/MS during instances where incomplete peptide fragmentation occurs. Identification of the labeled residue would permit the quantitation of the extent of phosphorylation for this residue, and hence protein, based on the measured peptide isotope ratio between the standard (control) and experimental sample, labeled with the isotopically light and heavy versions of the appropriate B-L-PhRG, respectively.

A. Method 1

Method 1 (outlined in FIG. 6) is designed to be performed in two steps. The first step involves activation of the phosphotyrosyl residue by incorporating an electron withdrawing group within the ring (Method 1, parts (a) and (b) of FIG. 6). The second step is selective nucleophilic aromatic substitution of the phosphate moiety on the ring using B-L-PhRG, where PhRG is the reacting nucleophile (Method 1, part (c) of FIG. 6).

Figure 6:
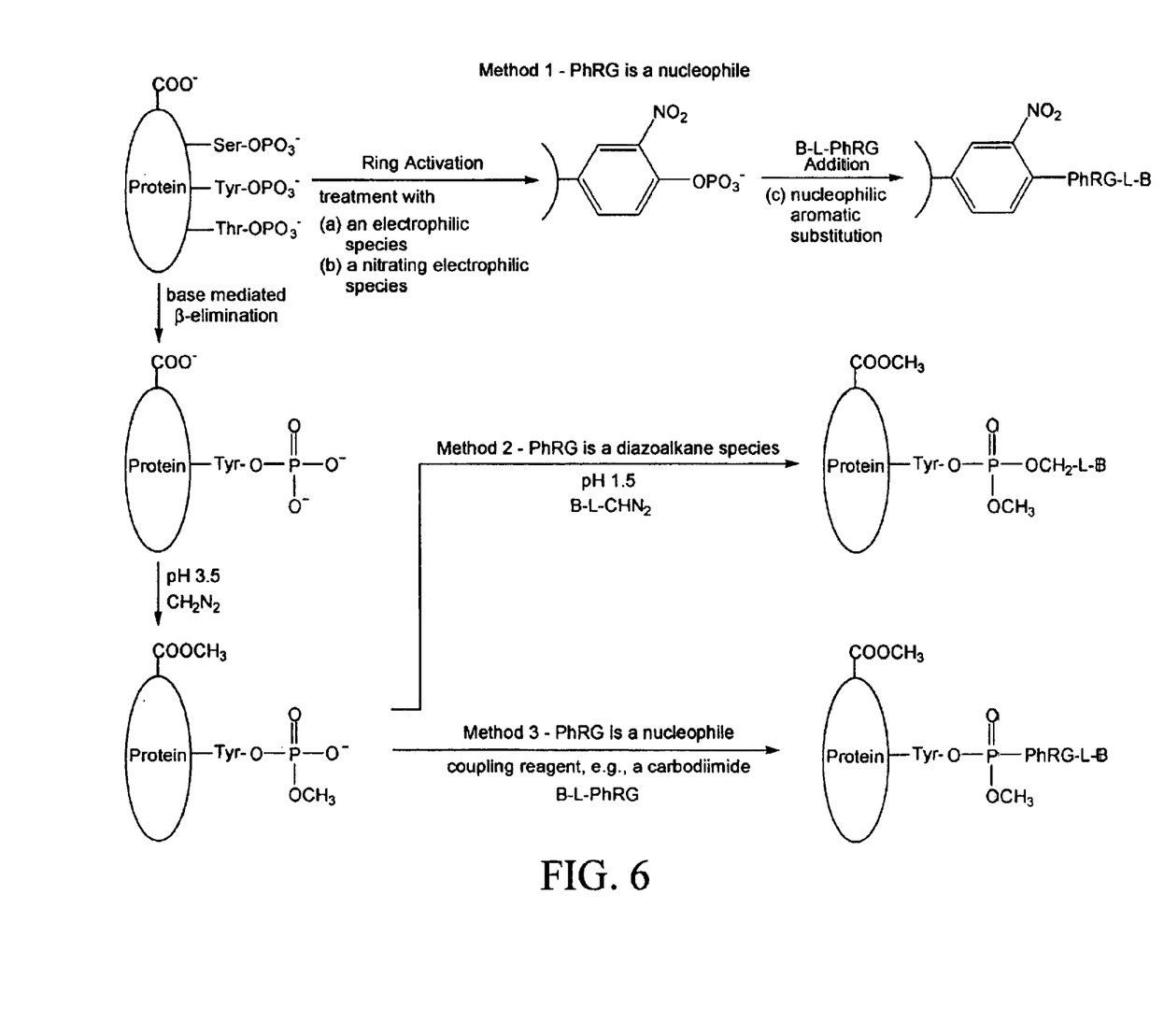
FIG. 6 shows various reaction schemes for the tagging of phosphotyrosine.

The sequence involving electrophilic aromatic substitution (Method 1, parts (a) and (b) of FIG. 6) involves initial treatment of the protein/peptide with an electrophilic reagent (such as methyl sulfate, methyl iodide, 9-anthryidiazomethane, 1-pyrenyldiazomethane, 4-(diazomethyl)-7-methoxycoumarin, and 4-(diazomethyl)-7-diethylaminocoumarin) under appropriate conditions (acidic methanol, at a pH of about 1.5–2.4, preferably about 1.9). Such manipulation serves to minimize the number of sites (such as SH, $NH_2$, OH and COOH) at which a species capable of electrophilic aromatic substitution (eg. a "$NO_2^+$" species) could potentially react. Reaction of a representative nitrating electrophilic species at sites both in the side chain of the protein (eg. aromatic and possibly basic residues) and potentially in the backbone (amide) are feasible. However, reaction at the activated ortho-position of the phosphotyrosine results in a unique derivative, one capable of nucleophilic aromatic substitution. Thus, Method 1 (FIG. 6) entails initial modification of the peptide with an electrophile capable of blocking the nucleophilic thiol, amine and hydroxyl moieties of the peptide (Method 1, part (a) of FIG. 6), followed by treatment with a nitrating species capable of electrophilic aromatic substitution (Method 1, part (b) of FIG. 6), and subsequent nucleophilic aromatic substitution of the phosphoryl nitroaromatic (Method 1, part (c) of FIG. 6). Suitable nitrating species for aromatic compounds include, nitric acid alone, or in water, acetic acid or acetic anhydride, methyl nitrate and $BF_3$, $NaNO_2$ and trifluoroacetic acid, $N_2O_4$ and nitronium salts such as $NO_2^+BF_4^-$, $NO_2^+PF_6^-$ and $NO_2^+ CF_3SO_3^-$.

B. Method 2

In this protocol (Method 2, FIG. 6), the phosphodiester of tyrosine is subjected to reaction with an electrophilic reagent such as B-L-PhRG where PhRG is a diazoalkane species, B-L-$CHN_2$, for example. After adjustment of the pH to approximately 1.5 the remaining phosphate site is protonated which enables reaction with the specific diazoalkane B-L-$CHN_2$.

C. Method 3

In a third method (Method 3, FIG. 6), the phosphodiester of tyrosine is coupled to B-L-PhRG, where PhRG is a nucleophile, using standard coupling methodology. A diversity of coupling procedures which produce a range of phosphodiester derivatives (eg., ester, thioester, amide) can be utilized depending upon the detection method to be used. Activation of the single remaining active phosphate tyrosine monoester can be achieved with an activating groups such as a carbodiimide, an anhydride, an alkyl chloroformate, pyridinium salts-$Bu_3N$, phenyl dichlorophosphate, $PhOPOCl_2$, DCC and an aminopyridine, 2-chloro-1,3,5-trinitrobenzene and pyridine, polyphosphate ester, chlorosulfonyl isocyanate, chlorosilanes, $MeSO_2Cl$-$Et_3N$, $Ph_3P$-$CCl_4$-$Et_3N$, and N,N'-carbonyidiimidazole. Attachment of B-L-PhRG can then be accomplished by the reaction of the activated phosphate with a nucleophilic PhRG moiety.

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

B-L-PhRG wherein B is a binding agent, L is a linker group having one or more atoms that are differentially labeled with one or more stable isotopes, and PhRG is a phosphate reactive group that selectively reacts with amino acid residues of the one or more proteins that were formerly phosphorylated;

reacting each sample with one of the protein reactive reagents to provide proteins bound to the protein reactive reagent, whereby such bound proteins are differentially labeled with stable isotopes;

capturing bound proteins of the samples using a capture reagent that selectively binds the binding agent of the protein reactive reagent;

releasing captured bound proteins from the capture reagent by disrupting the interaction between the binding agent and the capture reagent;

detecting the amount of released bound proteins; and comparing the amount of released bound proteins from one sample to the amount of released bound proteins from one or more other samples.

2. The method of claim 1, wherein the bound proteins in the samples are enzymatically or chemically processed to convert them into bound peptides.

3. The method of claim 1, wherein a protein portion of one or more of the bound proteins are sequenced by tandem mass spectrometry to identify the bound protein.

4. The method of claim 1, wherein the amount of one or more phosphorylated proteins in the sample is determined by mass spectrometry and further comprising introducing into a sample a known amount of one or more internal standards for each protein to be quantified.

5. The method of claim 1, wherein one or more phosphorylated amino acid residues are selected from the group consisting of threonine, serine, and tyrosine.

6. The method of claim 1, wherein the released bound proteins are separated by chromatography prior to detecting the bound proteins by mass spectrometry.

7. The method of claim 1, wherein a plurality of proteins are detected and identified in one or more of the two or more samples.

8. The method of claim 3, wherein all of the proteins in one or more of the two or more samples are identified.

What is claimed is:

1. A method of comparing the phosphorylation states of one or more proteins in two or more samples comprising:

providing a substantially chemically identical and differentially isotopically labeled protein reactive reagent for each sample wherein the protein reactive reagent satisfies the formula:

9. The method of claim 1, wherein the two or more samples are combined after being reacted with a protein reactive reagent and before the bound proteins of the samples are captured.

10. The method of claim 1, wherein the proteins being quantified are membrane proteins.

11. The method of claim 1, wherein different samples contain proteins originating from different organelles or different subcellular fractions.

12. The method of claim 9, wherein each of the two or more samples are taken at different times, or contain proteins expressed in response to different environmental or nutritional conditions, or different chemical or physical stimuli.

13. The method of claim 1, wherein the different samples represent proteins expressed in different disease states.

14. A method for screening for a therapeutic that alters a phosphorylation state of a protein, the method comprising:

contacting at least one test sample containing the protein with the therapeutic;

providing at least one control sample containing the protein;

removing one or more phosphate groups from one or more amino acid residues of the protein in the at least one test sample and the at least one control sample;

tagging the at least one test sample and the at least one control sample with substantially chemically identical and differentially isotopically labeled protein reactive reagents for each sample, wherein the protein reactive reagents satisfies the formula:

B-L-PhRG wherein B is a binding agent that selectively binds to a capture reagent, L is a linker group having one or more atoms that are differentially labeled with one or more stable isotopes, and PhRG is a phosphate reactive group that selectively reacts with amino acid residues that were formerly phosphorylated; and detecting a level of phosphorylation of the tagged proteins in the at least one test sample and the at least one control sample; and determining whether the therapeutic altered the level of phosphorylation of the tagged proteins in the at least one test sample.

15. A method of detecting different types of phosphorylated amino acid residues in one or more proteins, the method comprising:

providing one or more samples containing one or more proteins;

removing the phosphate group from at least one serine residue or at least one threonine residue of at least one protein in each sample;

removing the phosphate group from at least one tyrosine residue of at least one protein in each sample;

tagging the at least one serine residue or the at least one threonine residue with substantially chemically identical and differentially isotopically labeled protein reactive reagents for each sample, wherein the protein reactive reagents satisfies the formula:

B-L-PhRG wherein B is a binding agent that selectively binds to a capture reagent, L is a linker group having one or more atoms that are differentially labeled with one or more stable isotopes, and PhRG is a phosphate reactive group that selectively reacts with amino acid residues that were formerly phosphorylated;

tagging the at least one tyrosine residue with substantially chemically identical and differentially isotopically labeled protein reactive reagents for each sample, which are differentially isotopically labeled relative to the protein reactive reagents used to tag the at least one serine residue of the at least one threonine residue, wherein the protein reactive reagents satisfies the formula:

B-L-PhRG wherein B is a binding agent that selectively binds to a capture reagent, L is a linker group having one or more atoms that are differentially labeled with one or more stable isotopes, and PhRG is a phosphate reactive group that selectively reacts with amino acid residues that were formerly phosphorylated; and detecting the tagged amino acid residues.

16. The method of claim 15, wherein the removing the phosphate group from at least one serine residue or at least one threonine residue is after the removing the phosphate group from at least one tyrosine residue.

17. The method of claim 15, wherein tagging the at least one serine residue or the at least one threonine residue is done after the tagging the at least one tyrosine residue.

18. The method of claim 17, wherein the removing the phosphate group from at least one serine residue or at least one threonine residue is after the removing the phosphate group from at least one tyrosine residue.

* * * * *

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Test Peptide

<400> SEQUENCE: 1

Phe Gln Ser Glu Glu Gln Gln Gln Thr Glu Asp Glu Leu Gln Asp Lys
 1               5                  10                  15